United States Patent
Wollenweber et al.

(10) Patent No.: US 6,764,979 B2
(45) Date of Patent: Jul. 20, 2004

(54) AQUEOUS HERBICIDAL AGENT

(75) Inventors: Horst-Werner Wollenweber, Hamburg (DE); Hans-Georg Mainx, Leichlingen (DE); Benoit Abribat, Dannemols (FR); Hans De Ruiter, Wageningen (NL)

(73) Assignee: Cognis Deutschland GmbH & Co. KG, Duesseldorf (DE)

( * ) Notice: Subject to any disclaimer, the term of this patent is extended or adjusted under 35 U.S.C. 154(b) by 41 days.

(21) Appl. No.: 10/257,698

(22) PCT Filed: Apr. 3, 2001

(86) PCT No.: PCT/EP01/03778

§ 371 (c)(1),
(2), (4) Date: Feb. 20, 2003

(87) PCT Pub. No.: WO01/76368

PCT Pub. Date: Oct. 18, 2001

(65) Prior Publication Data

US 2003/0158044 A1 Aug. 21, 2003

(30) Foreign Application Priority Data

Apr. 12, 2000 (DE) .......................... 100 18 159

(51) Int. Cl.⁷ .................... A01N 25/30; A01N 37/34
(52) U.S. Cl. ..................... 504/310; 504/358
(58) Field of Search ................. 504/310, 358

(56) References Cited

U.S. PATENT DOCUMENTS

| | | | |
|---|---|---|---|
| 2,678,935 A | 5/1954 | Sundberg et al. | 260/410.6 |
| 3,539,518 A | 11/1970 | Feighner et al. | 252/89 |
| 4,022,808 A | 5/1977 | Yoshihara et al. | 260/410.6 |
| 5,021,083 A * | 6/1991 | Schapira et al. | 71/105 |
| 5,292,910 A | 3/1994 | Raths et al. | 554/149 |

FOREIGN PATENT DOCUMENTS

| | | |
|---|---|---|
| DE | 29 24 403 A1 | 12/1980 |
| DE | 268 147 A1 | 5/1989 |
| EP | 0 228 943 A | 7/1987 |
| EP | 0 485 207 B1 | 5/1992 |
| GB | 1050497 A | 12/1966 |
| WO | WO 90/13533 A1 | 11/1990 |
| WO | WO 91/15441 A1 | 10/1991 |
| WO | 00/51427 * | 9/2000 |

OTHER PUBLICATIONS

Römpp Lexikon Chemie, 10th Edition, (1997), p.1764.

* cited by examiner

Primary Examiner—S. Mark Clardy
(74) Attorney, Agent, or Firm—Aaron R. Ettelman

(57) ABSTRACT

A herbicidal agent comprising: (1) water; (2) ioxynil and/or a derivative thereof; (3) a compound of the formula (I)

$$RO—(CH_2H_4O)_n(CH_3H_6O)_m—R' \qquad (I)$$

wherein RO is an alcohol radical selected from the group consisting of branched or linear, saturated or unsaturated monohydric alcohols having from 1 to 6 carbon atoms, or a polyol radical having from 2 to 12 carbon atoms and from 2 to 6 hydroxyl groups; R' is hydrogen or an ester group —CO—R" wherein R" is a branched or linear, saturated or unsaturated alkyl radical having 5 to 29 carbon atoms, n is a number between 1 and 50 and m is zero or a number between 1 and 10. The herbicidal agents permit high penetration of the herbicide into the plant.

13 Claims, No Drawings

AQUEOUS HERBICIDAL AGENT

The present invention relates to aqueous herbicidal agents which comprises at least one agrochemical active ingredient from the group consisting of ioxynil and derivatives thereof, and certain alkoxylated fatty acid esters, to the use of such fatty acid esters for increasing the penetration of ioxynil or derivatives thereof into the leaves of plants, and to a method of controlling undesired plant growth.

To control weeds, a large number of herbicidal substances are known which frequently exhibit only low or no solubility in water. An important representative is ioxynil (3,5-diiodo-4-hydroxybenzonitrile) and derivatives thereof. During application of these active ingredients, the low solubility in water means that penetration into the plant is only low and thus the herbicidal action is inadequate. Such agrochemical active ingredients are therefore formulated in the form of an aqueous dispersion or emulsion and can then be used without problems, e.g. by spraying onto the plants, where the emulsifier also functions as a wetting agent and permits improved uptake of the active ingredient into the plant. The higher the penetration of the active ingredient, the more effectively and efficiently it can be used. There is therefore generally a need for formulations which permit the greatest possible penetration of the herbicidal active ingredient into the plant. DE-A 29 24 403 discloses, for example, aqueous agents which comprise ioxynil salts and, as formulation auxiliaries, alkali metal salts of alkyl polyglycol ether phosphate partial esters. EP-0-485 207 discloses aqueous emulsions comprising ioxynil octanoate and heptanoate which comprise polyalkylene oxide-modified silanes or ethoxylated tall oil amides as emulsifiers. Surprisingly, it has been found that aqueous agents which comprise ioxynil or derivatives thereof and, as emulsifiers, certain alkoxylated alcohols permit very high penetration of the herbicide into the plant.

The present application therefore provides aqueous agents which comprise ioxynil or derivatives thereof and one or more compounds of the general formula (I)

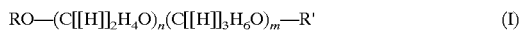

$$RO-(C[[H]]_2H_4O)_n(C[[H]]_3H_6O)_m-R' \quad (I)$$

in which RO is an alcohol radical chosen from the group of branched or linear, saturated or unsaturated monohydric alcohols having 1 to 6 carbon atoms, or polyols having 2 to 12 carbon atoms and 2 to 6 hydroxyl groups, and R' is hydrogen and/or a group —CO—R", in which R" is a branched or linear, saturated or unsaturated elkyl radical having 5 to 29 carbon atoms, n is a number between 1 and 50 and m is zero or a number between 1 and 10.

DETAILED DESCRIPTION OF THE INVENTION

The agents according to the invention comprise loxynil and/or derivatives thereof, preferably ioxynil alkyl esters or sodium salts and/or potassium salts of ioxynil or sulfates and carbonates thereof. Particular preference is given to agents which comprise ioxynil octanoate or heptanoate.

The alkoxylated compounds of the formula (I) are known substances which are described, for example, in U.S. Pat. Nos. 2,678,935, 3,539,518, 4,022,808 or GB 1,050,497, the disclosure of which also forms part of the present application.

The compounds of the formula (I) can be prepared by all methods known to the person skilled in the art, e.g. by esterification of fatty acids with alkoxylated methanol, as U.S. Pat. No. 3,539,518 describes. This process is, however, associated with a number of disadvantages, it proceeds in two stages, the esterification lasts for a very long time and the products are colored as a result of the high reaction temperatures. In addition, fatty acid methyl ester ethoxylates prepared in this way have relatively high OH numbers after esterification, which may be problematic for some applications. A further possibility involves the direct reaction of fatty acid esters with alkylene oxides in the presence of transition metal catalysts, as described in U.S. Pat. No. 4,022,808. Preferably, however, the fatty acid alkyl ester alkoxylates are prepared by a heterogeneously catalyzed direct alkoxylation of fatty acid alkyl esters with ethylene oxide and/or propylene oxide over calcined or hydrophobicized hydrotalcites. This synthesis process is described in detail in the laid-open specifications WO 90/13533 and WO 91/15441, the disclosure of which also forms part of the present application. The products which form in the processes are characterized by a low OH number, the reaction is carried out in one stage and pale-colored products are obtained. The fatty acid alkyl esters which serve as starting materials can be obtained either from natural oils and fats, or be prepared by a synthetic route.

The alkoxylated fatty acid esters contain at least 1 mol of ethylene oxide groups per mole of ester. Preference is given to compounds of the formula (I) which, per mole of ester, contain 1 to 30 mol of ethylene oxide. It is preferred that, in addition to the ethylene oxide units, between 1 and 10 propylene oxide groups are also present in the molecule. Preference is also given to those compounds of the formula (I) which contain between 1 and 30 mol of ethylene oxide per mole of ester and 1 to 10 mol of propylene oxide groups. For these mixed ethylene/propylene oxide adducts, it is possible to use either those compounds which have been reacted with a mixture of ethylene oxide and propylene oxide, or else compounds which have been reacted in two separate steps with ethylene oxide and propylene oxide. The alkoxides spread themselves randomly over the OH groups present depending on the preparation process.

If compounds of the formula (I) are used which contain polyols as alcohol radical RO, then the data relating to the amount of ethylene oxide or propylene oxide units (indices n and m) always relates to the overall molecule. The exact distribution of the ethylene oxide and propylene oxide units on the different hydroxyl groups of the polyol depends, however, as is known, on the synthesis process.

The fatty acid ester radicals —CO—R" contain alkyl radicals R" having 5 to 29 carbon atoms. Suitable as fatty acid component are natural or synthetic fatty acids, in particular straight-chain, saturated or unsaturated $C_6$-$C_{30}$ fatty acids, including technical-grade mixtures thereof, as are obtainable by fat cleavage from animal and vegetable fats and oils, e.g. from coconut oil, palm kernel oil, soybean oil, sunflower oil, rapeseed oil, cotton wool seed oil, fish oil, beef tallow and lard; specific examples are caprylic, capric, lauric, lauroleic, myristic, myristoleic, palmitic, palmitoleic, oleic, elaidic, arachidic, gadoleic, behenic and erucic acid.

Suitable as alcohol component RO are straight-chain or branched, saturated or unsaturated monohydric alcohols having 1 to 6 carbon atoms, e.g. methanol, ethanol, n- and i-propanol, n- and i-butanol, pentanol, hexanol, 2-ethylhexanol and cyclohexanol. Examples of polyols having 2 to 6 carbon atoms which can be used are ethylene glycol, 1,2-propylene glycol, 1,2-butylene glycol glycerol or trimethylolpropane and pentaerythritol.

In principle, all of the hydroxyl groups of the alcohols are substituted by the alkoxides, although not all of the terminal alkoxide radicals are capped with ester groups. If polyols are used as starting alcohol components RO, such as glycerol or ethylene glycol, the agents can therefore contain either compounds of the formula (I) which are obtained by reaction of the full esters and also of the partial esters with alkoxides. Preference is, however, given to those compounds of the formula (I) in which all of the hydroxyl groups of the alcohols are alkoxylated and also all terminal alkoxide groups are capped with ester groups of the formula —CO—R". In these preferred compounds, the radical R" in the formula (I) is therefore exclusively a branched or linear, saturated or unsaturated alkyl radical having 5 to 29 carbon atoms.

In the agents according to the invention, preference is also given to using those alkoxylated fatty acid esters of the formula (I) whose fatty acid component is chosen from linear, unbranched C6 to $C_{18}$ fatty acids and whose alcohol component is methanol, where these esters of the formula (I) preferably contain between 1 and 3 mol of propylene oxide and between 1 and 6 mol of ethylene oxide per mole of ester. Such compounds can be obtained, for example, by the above-described reaction of palmitic, stearic, oleic, linoleic or linolenic acid lauric and myristic acid and esters thereof with alkoxides.

Also suitable are alkoxylated compounds in which the alcohol component used is glycerol and the fatty acid component is chosen from saturated or unsaturated, branched or unbranched fatty acids having 18 to 22 carbon atoms and the esters contain between 1 and 3 mol of ethylene oxide per mole of ester. Particular preference is given to compounds of the formula (I) in which n is 5,10 or 30 and m is zero. Such compounds can be obtained, for example, by the reaction of glycerol esters of natural fatty acids, such as, for example, palm oil, rapeseed oil, soybean oil or, preferably, castor oil, with ethylene oxide.

The compounds of the formula (I) present in the agents according to the invention are nonionic compounds which can additionally also be characterized by their HLB value (hydrophilic-lipophilic balance according to the definition by Griffin; see Römpp Lexikon Chemie, 10th edition 1997, page 1764). Preference is given to those agents which comprise compounds of the formula (I) with HLB values between 4 and 10 and in particular between 5 and 9.

The agents comprise, as herbicidal active ingredients, at least ioxynil or derivatives thereof, although mixtures with other different active ingredients are also possible. The agents according to the invention can comprise the active ingredient either in enriched form, i.e. the agents are concentrates with more than 50% by weight to a maximum of 90% by weight of active ingredient. They can, however, also be in dilute form. Preference is given to agents which comprise between 0.01 and 5% by weight of ioxynil or derivatives thereof, based on the weight of the agent. If other agrochemical active ingredients are present, then these are present in amounts of from 0.01 to 10% by weight. The proportion of water in the agents according to the invention is preferably between 10 and 99.9% by weight. The quantitative ratio between the compounds of the formula (I) and the active ingredients is preferably between 1:1 and 1:100. Particular preference is given to those agents in which the weight ratio between the compounds of the formula (I) and the active ingredients is in the range from 1:10 to 1:80 and in particular in the range from 1:2 to 1:5.

In addition to ioxynil and derivatives thereof and the compounds of the formula (I), the aqueous agents according to the invention can also comprise further customary ingredients and additives. These include solvents, such as ethylene or propylene glycols and $C_1$-$C_6$-alcohols, solid carriers, such as lignin, lignin derivatives or clays and further known emulsifiers or dispersants. Particular preference, however, is given to those agents which comprise exclusively emulsifiers of the formula (I) and otherwise comprise no further emulsifiers or dispersants. Particular preference is given to those agents which are free from colloids, such as titanium dioxide, and/or are free from solvents, in particular from mineral oil-based solvents.

The agents according to the invention are storage-stable even at temperatures greater than 30° C. and can be prepared without the action of high shear forces, for example by manual stirring. The agents according to the invention form without the application of strong shear forces, e.g. by simple stirring by hand. The compounds of the formula (I) can be initially introduced for this purpose, for example, in liquid form. The active ingredient is then added and this mixture is dispersed in water. If compounds of the formula (I) with melting points above room temperature are used, they can be used in molten form. It is, however, preferable to use those compounds of the formula (I) which have a melting point below 25° C. It is, however, also possible firstly to prepare a mixture of the agrochemical active ingredient in water, and then to emulsify or disperse this mixture by adding compounds of the formula (I).

Also claimed is a method for controlling undesired plants, where an aqueous ioxynil-containing agent as in the above description is applied to the leaves of plants by any method known to the person skilled in the art in amounts such that the plants die.

The present invention further provides for the use of the compounds of the formula (I) for increasing the penetration of ioxynil or derivatives thereof into the leaves of plants.

EXAMPLES

Six aqueous ioxynil Na salt emulsions were prepared which were either free from emulsifiers or comprised known emulsifiers, and these were compared with an agent according to the invention comprising, as additive, a compound of the formula (I) where RO=glycerol, R'=COR" where R"=C16–C18, m=0, n=30.

The emulsifiers were in each case present in amounts of 0.5% by weight, based on the overall agent. The concentration of the sodium salt of ioxynil was 4.1 mM. In each case 0.1 µl of the aqueous agent were applied to the first leaves of deadly nightshade. Penetration into the leaves after 24 hours was then measured. The results are given in Table 2.

TABLE 1

| Experiment | Emulsifier |
| --- | --- |
| (1) | — |
| (2) | $C_{6-10}$-alkyl (oligo) glucoside |
| (3) | $C_{6-10}$ fatty acid methyl ester + 3 EO |
| (4) | $C_{8-10}$ fatty acid methyl ester + 6 EO |
| (5) | nonylphenol + 10 EO |
| (6) | triglyceride according to the invention |

TABLE 2

| Experiment | Penetration after 24 hours in % |
| --- | --- |
| (1) | 0 |
| (2) | 2 |
| (3) | 22 |
| (4) | 56 |
| (5) | 42 |
| (6) | 82 |

The results show the increase in the penetration of the ioxynil as a result of the addition of the agent according to the invention.

What is claimed is:

1. A method of increasing the penatration of ioxynil or a derivative thereof into the leaves of a plant comprising the steps of: (1) forming a composition comprising water and ioxynil and/or a derivative thereof and a compound of the formula (I)

wherein RO is an alcohol radical selected from the group consisting of branched or linear saturated or unsaturated monohydric alcohols having from 1 to 6 carbon atoms, or a polyol radical having from 2 to 12 carbon atoms and from 2 to 6 hydroxyl group; R' is hydrogen or an ester group —CO—R" wherein R" is a branched or linear, saturated or unsaturated alkyl radical having 5 to 29 carbon atoms, n is a number between 1 and 50 and m is zero or a number between 1 and 10 wherein the amount of the compound at formula I is sufficient to increase the penetration of ioxynil or derivatives thereof into the leaves of a plant; (2) contacting the leaves of a plant with the composition.

2. The method of claim 1 wherein R" is branched or linear, saturated or unsaturated alkyl radical having from 17 to 21 carbon atoms.

3. The method of claim 1 wherein RO is a glycarol radical and R" is a branched or linear, saturated or unsaturated alkyl radical having from 17 to 21 carbon atoms.

4. The method of claim 1 wherein n is a number between 1 and 30 and m is zero or a number between 1 and 5.

5. The method of claim 1 wherein n is 5,10 or 30 and m is zero.

6. The method of claim 1 wherein —CO—R" is a ricinoleic acid radical and RO is a glycerol radical.

7. The method of claim 1 wherein RO is a methanol radical and R" is a branched or linear, saturated or unsaturated alkyl radical having from 5 to 17 carbon atoms.

8. The method of claim 1 wherein the compounds of the formula (I) has an HLB value between 4 and 10.

9. The method of claim 1 wherein the amount of the ioxynil is from 0.01 to 5% by weight.

10. The method of claim 1 wherein the ioxynil derivative is an alkyl esters.

11. The agent of claim 10 wherein the ioxynil derivative is ioxynil octanoate or ioxynil heptanoate.

12. The method of claim 1 wherein the ioxynil derivative is the sodium salts and/or potassium salt.

13. The method of claim 1 is wherein the agent is free from colloidal material.

* * * * *